United States Patent [19]

Long

[11] Patent Number: 4,619,149
[45] Date of Patent: Oct. 28, 1986

[54] BELT CONVEYOR CROSS-STREAM SAMPLING SYSTEM

[76] Inventor: John B. Long, 421 Heron Hill Dr., Louisville, Tenn. 37777

[21] Appl. No.: 688,394

[22] Filed: Jan. 2, 1985

[51] Int. Cl.$^4$ .......................... G01N 1/12; G01N 1/20
[52] U.S. Cl. ................................ 73/863.91; 73/864.32
[58] Field of Search ........... 73/863.91, 863.92, 864.31, 73/864.32, 863.01, 863

[56] References Cited

U.S. PATENT DOCUMENTS

| | | | |
|---|---|---|---|
| 2,889,709 | 6/1959 | Blyth | 73/863.91 |
| 3,181,369 | 5/1965 | Taylor | 73/863.91 |
| 3,280,635 | 10/1966 | Cochet | 73/863.91 |
| 3,487,427 | 12/1969 | Cahill | 73/863.91 |
| 3,545,280 | 12/1970 | Gosney | 73/863.91 |
| 3,791,218 | 2/1974 | Pennington | 73/863.91 X |
| 3,881,356 | 5/1975 | Palm | 73/863.91 |
| 4,133,210 | 1/1979 | Jaeger | 73/863.91 X |

FOREIGN PATENT DOCUMENTS

| | | | |
|---|---|---|---|
| 1002135 | 8/1965 | United Kingdom | 73/863.91 |
| 742752 | 6/1980 | U.S.S.R. | 73/863.91 |

OTHER PUBLICATIONS

Tema–Siebtechnik advertisement p. 17, CQ Fall 1983.
Tema–Siebtechnik brochure "Automatic Mechanical Sampling Systems", Bulletin 8301; 1983; 6 pages.
Tema–Siebtechnik Sampling System Reference List; 5 pages by Jul. 1985.
"Tema–Siebtechnik Automatic Hammer Sampler Systems" publication by Jul. 1985; 17 pages.
Bristol Engineering Company Bulletin 101 entitled "Bristol DS Series Automatic Samplers for Conveyor–Handled Bulk Products"; 4 pages; 1977.
Bristol Engineering Company Bulletin 163 entitled "Bristol DS-3 Series Heavy Duty Belt Samplers"; 2 pages; by Jul. 1985.
James A. Redding Company brochure; 22 pages; by Jul. 1985.
MSI Mine Systems Inc. brochure entitled "Truck Sampling System"; 4 pages; Oct. 1983.
Ramsey Engineering Co. brochure; 4 pages; by Jul. 1985.
HSS Co. brochure "Select Sampling Systems"; 3 pages; by Jul. 1985.

*Primary Examiner*—Stewart J. Levy
*Assistant Examiner*—Tom Noland
*Attorney, Agent, or Firm*—Luedeka & Neely

[57] ABSTRACT

A method and apparatus are provided for cross-stream sampling of bulk material on a belt conveyor. The cross-stream sampling apparatus disclosed includes sample taking elements movable across the conveyor for removing a cross-stream increment of bulk material and contour elements for modulating the normal troughing of the conveyor belt and supporting and conforming the conveyor belt to the operative course of the sample taking elements as it moves across the conveyor belt. One form of the method includes segregating a cross-stream sample increment of the bulk material and sweeping the segregated increment from the conveyor belt and supporting and conforming the conveyor belt to the operative course of segregation and sweeping.

14 Claims, 13 Drawing Figures

BELT CONVEYOR CROSS-STREAM SAMPLING SYSTEM

BRIEF BACKGROUND, FIELD AND OBJECTIVES OF THE INVENTION

This invention relates to improvements in the mechanized sampling of bulk materials. In particular, to a system for taking a cross-stream sample of bulk materials from a conveying line.

The invention was primarily developed for use in the incremental collection of samples of coal from a conveyor line, and it is therefore convenient to describe the same as used for such purposes. Of course, the invention may be used in the sampling of various bulk materials and is not to be in any way construed as limited to the sampling of such as coal and coke.

It is apparent that a coal user wants and expects that coal shipped to him by a supplier have certain characterisitcs as to size, combustion, moisture content, BTU output, etc., in accordance with the needs of the user. Thus, a supply contract may provide for representative sampling of the coal shipment by the supplier, at the source, and by the user, on delivery. Since the respective sampling occurs at different times, at different places, and frequently according to different procedures, there is sometimes disagreement between the user and supplier as to the representative nature of the samples taken by the supplier. It would obviously be mutually advantageous for the user and supplier to agree upon use of a particular sampling system that would be accepted by the user as providing a representative sampling of the coal shipment.

Coal is one of the most difficult of materials to sample, a given conveying stream thereof including both small and large lumps, of various size and shape, down to dust size particles, and of varying composition, from particles that are noncombustible to those which can be burned completely.

Coal sampling is made even more difficult in that belt conveyors are most usually used for the conveying lines of coal handling facilities. The conveyor belt of such belt conveyors is typically supported on a plurality of spaced apart three roll idlers. The conveying surface of the conveyor belt thus presents faces that are angled with respect to one another and, since such belts are flexible, they will flex under sampling sweep arm pressures, making it difficult to remove a complete cross-stream sample therefrom. Also, since the belts of such belt conveyors have limited impact load capabilities, a sweep arm moving cross-stream for taking of a sample therefrom has a tendency to impact against and drive coal segments into the belt in a manner likely to puncture the belt.

An object of this invention is the provision of a contour means for modulating the normal troughing of a conveyor belt and supporting and conforming the same for facile removal of a cross-stream increment of bulk material therefrom.

The American Society for Testing Materials (ASTM), a recognized standards authority, provides certain designations to be used for sampling specifications, as follows:

Types of Increments:
Type I, in which specific pieces or portions are not subject to selection on a discretionary basis;
Type II, in which some measure of human discretion is exercised in the selection of specific pieces of coal or of specific portions of the stream, pile, or shipment;

Conditions of Increment Collection:
Condition A (Stopped-Belt Cut), in which a loaded conveyor belt is stopped and a full cross-section cut with parallel sides is removed from the coal stream. The distance between the parallel faces shall not be less than three times the diameter of the largest piece.
Condition B (Full-Stream Cut), in which a full cross-section cut is removed from a moving stream of coal.
Condition C (Part-Stream Cut), in which a portion, not a full cross stream, is removed from a moving stream of coal.
Condition D (Stationary Coal Sampling), in which a portion of coal is collected into a pile, a rail car, a barge, or a shiphold.

Spacing of Increments:
Systematic Spacing, in which the movements of individual increment collection are spaced evenly in time or in position over the lot.
Random Spacing, in which the increments are spaced at random in time or in position over the lot.

The ASTM specifies that the best possible increment is a full cross-section cut removed from a stopped belt. That is, a "Type I" increment, collected according to "Condition A", at "Systematic Spacing" intervals.

I am aware that others have provided various apparatus for sampling of bulk materials from a conveying line. For instance, as shown by U.S. Pat. No. 2,889,709, a "Condition C" increment collection; U.S. Pat. No. 3,280,635, a "Condition C" increment collection; U.S. Pat. No. 3,487,427, which does not appear to fall within any ASTM condition of increment collection; U.S. Pat. No. 3,791,218, a "Condition C" increment collection; and U.S. Pat. No. 4,133,210, a "Condition C" increment collection.

Until development of the present invention, all mechanized samplers have been of the ASTM "Condition B" or "Condition C" categories. I do not know of any previously provided mechanized stopped belt sampler according to the ASTM "Condition A".

Accordingly, a further object of this invention is the provision of a system for the mechanized sampling of bulk materials from a stopped belt conveyor in which the specific pieces or portions are not subject to selection on a discretionary basis; in which the loaded conveyor belt is stopped and a full cross-section cut with parallel sides is removed from the conveyor stream; and in which the movements of individual increment collection are spaced evenly in time or position over the lot.

Belt conveyors in use by coal handling facilities run from a length of less than a hundred feet to more than a thousand feet, the belt width of which may be from eighteen to ninety-six inches, and the belt speed of which may be from approximately four hundred feet per minute to approximately a thousand feet per minute. It is obvious that it would not be practical to intermittently stop a lengthy high-capacity belt conveyor for sampling purposes. Thus, as a mechanized stopped belt sampler, my invention will generally be used in connection with belt conveyors having a length of one hundred feet or less and having a belt width of forty-two inches or less.

My invention may also be adapted for taking a "Condition B" sample, that is, one in which a full cross-section cut is removed from a moving stream.

DETAILED DESCRIPTION OF THE INVENTION

Figure 11:
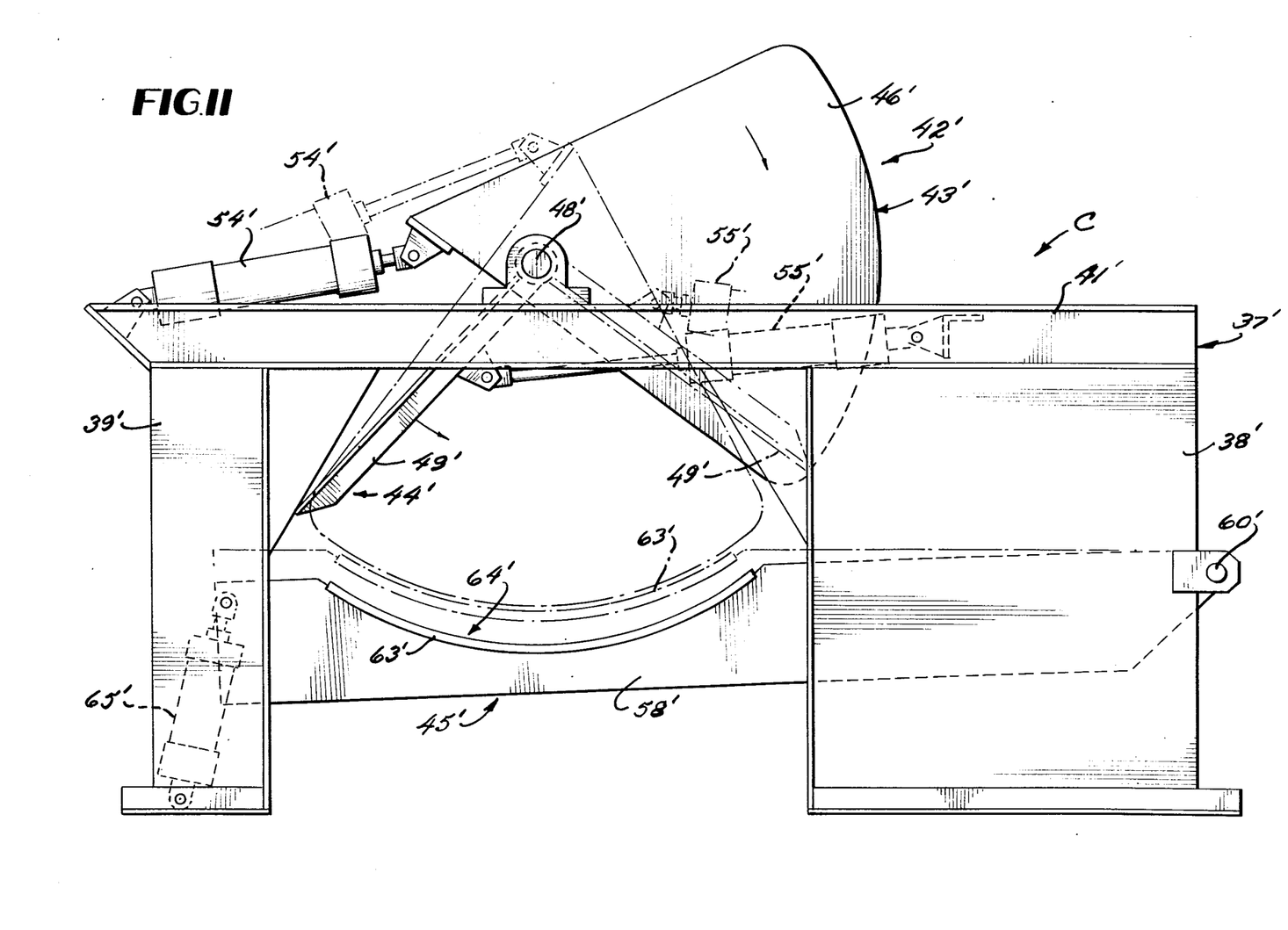
FIG. 11 is a side view of a modified form of my belt sampler.
Figure 12:
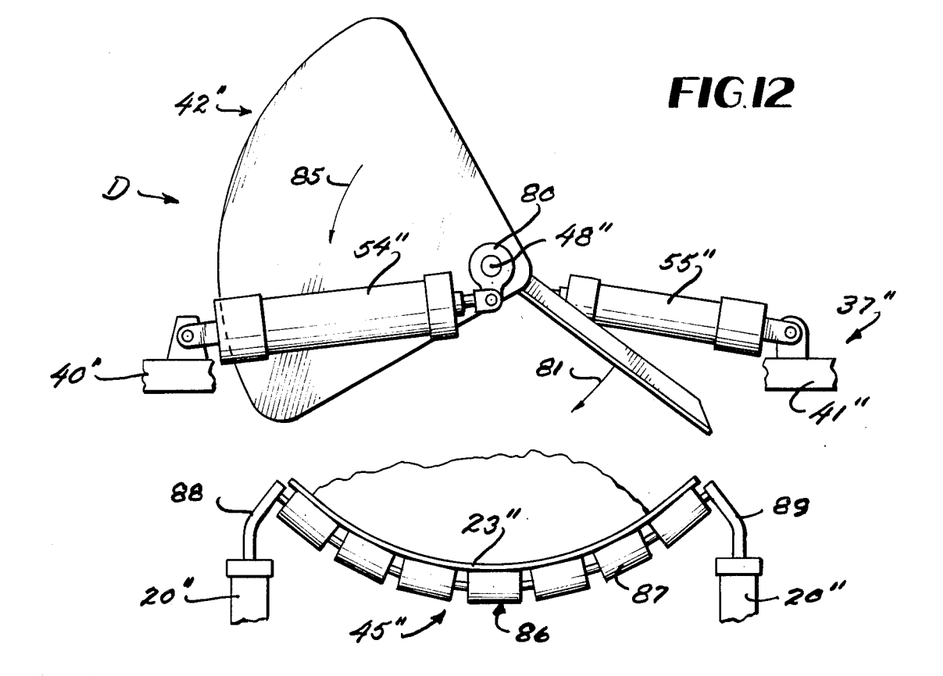
FIGS. 12 and 13 are diagrammatic views showing a further modified form of the invention.
Figure 13:
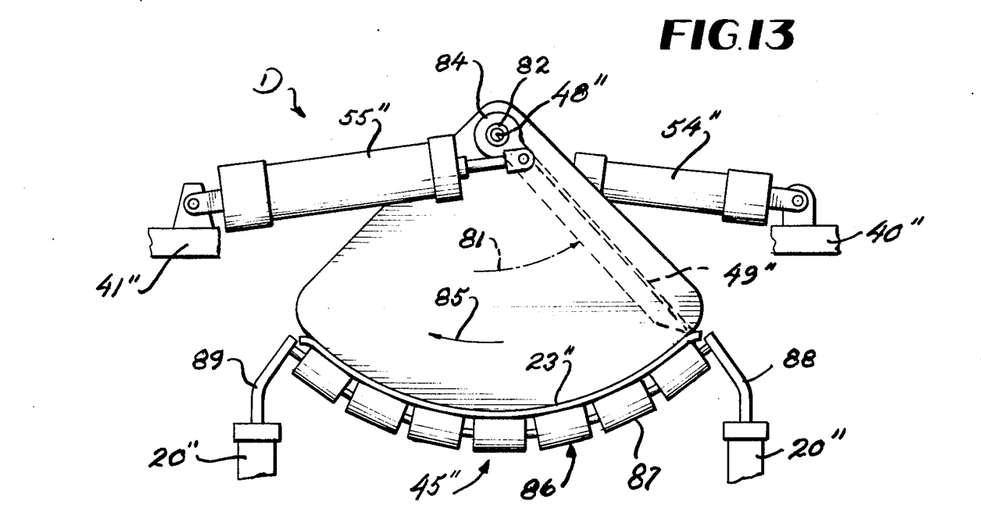

In the drawings, wherein are shown preferred and modified forms of the invention, and wherein similar reference characters designate corresponding parts throughout the several views, the letter A may generally designate a belt conveyor; B the belt sampler as shown in FIGS. 1–10; C the belt sampler as shown in FIG. 11, and D the belt sampler as shown in FIGS. 12 and 13.

Figure 1:
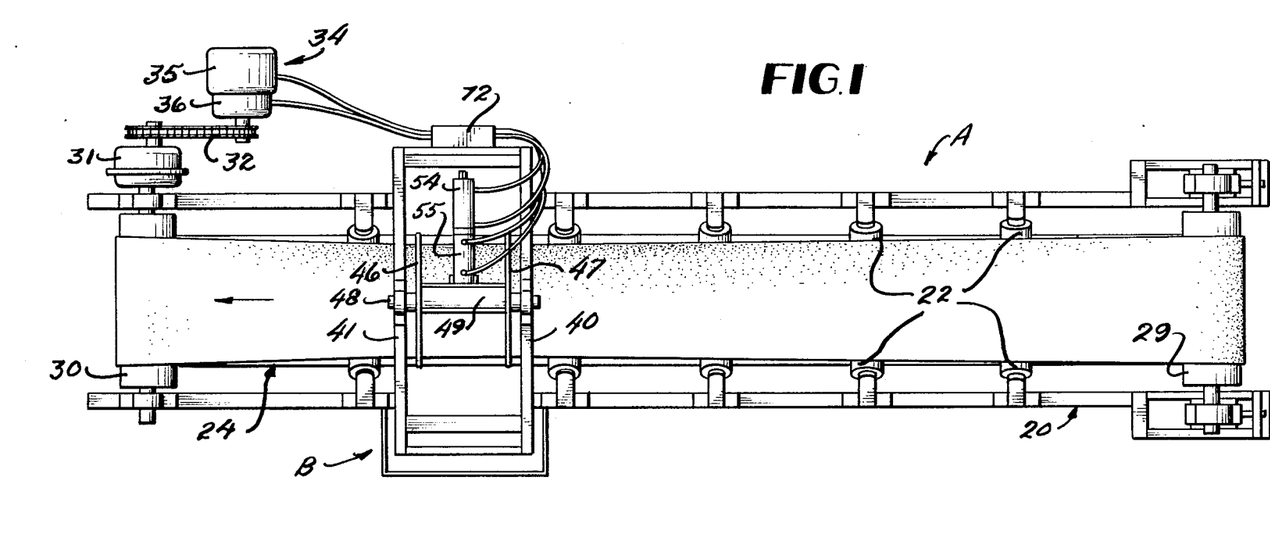
FIG. 1 is a top plan view of a belt conveyor which includes my improved belt sampler.
Figure 2:
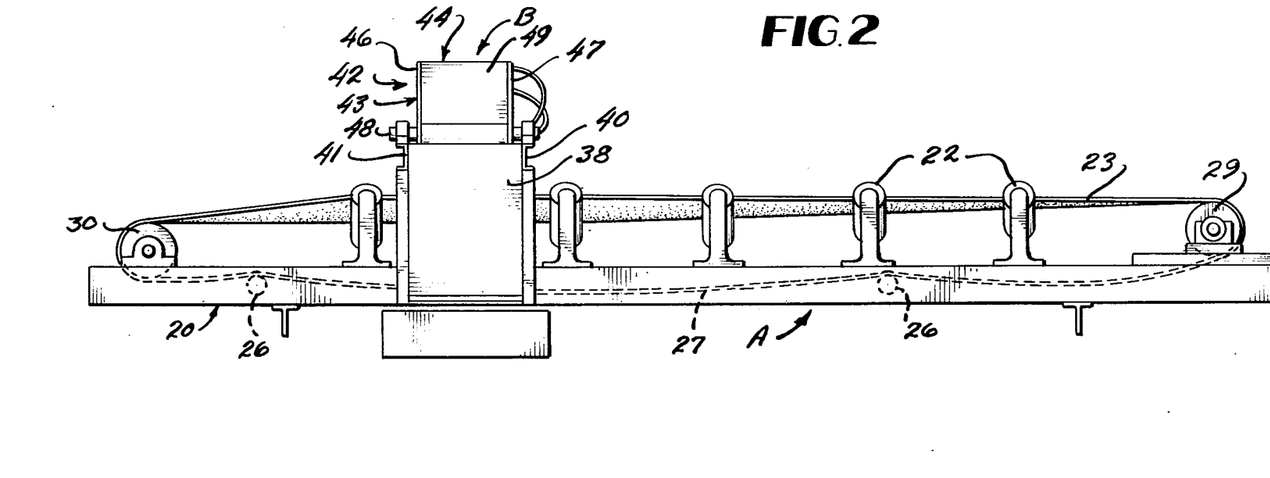
FIG. 2 is a side view of the belt conveyor of FIG. 1.
Figure 3:
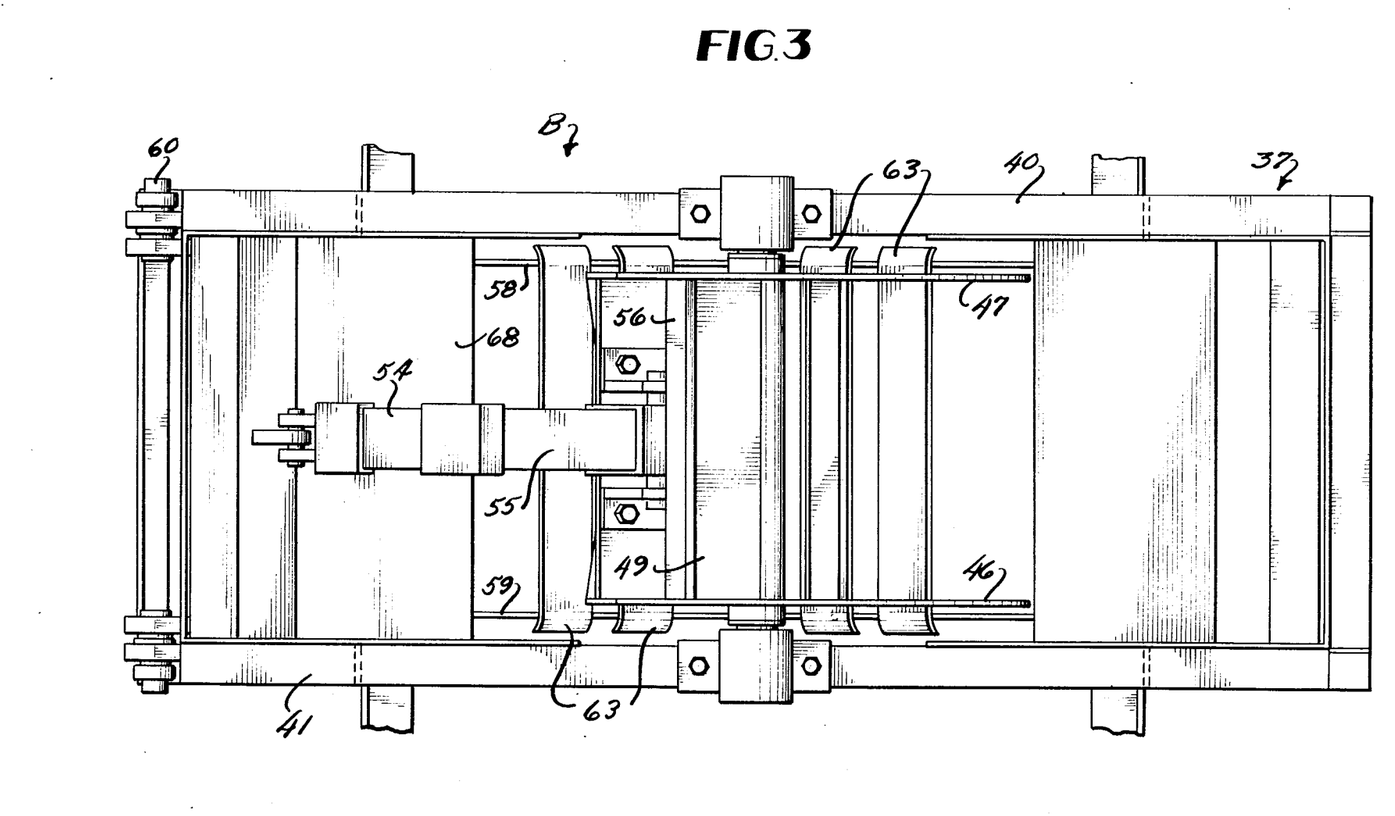
FIG. 3 is a top plan view of my improved belt sampler.
Figure 4:
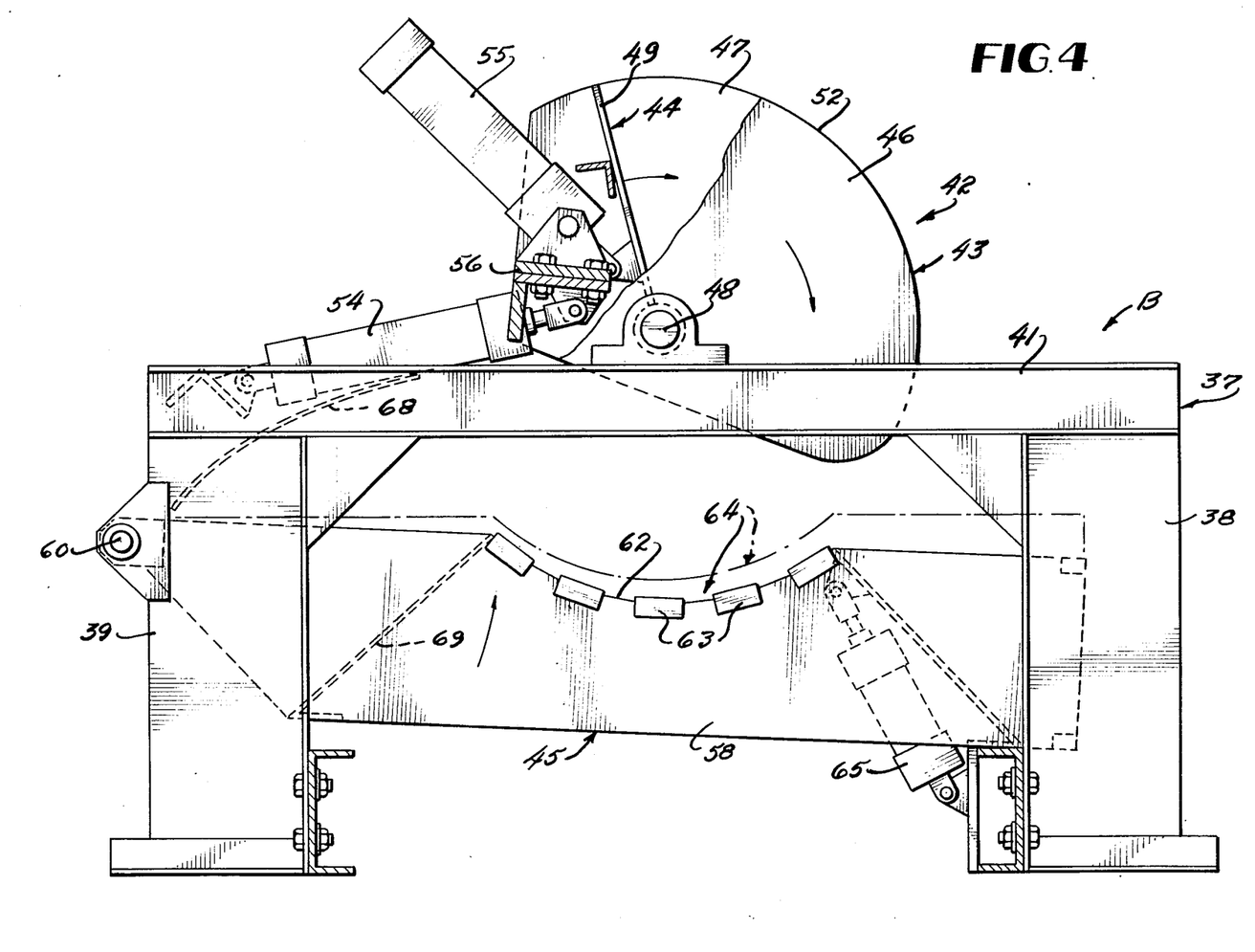
FIG. 4 is a side view of the belt sampler of FIG. 3, with parts thereof broken away to show the detail of parts thereof.

Belt conveyor A is representative of a typical belt conveyor, and may include a frame 20 on which may be mounted a plurality of idlers 22 for supporting the conveying reach 23 of a conveyor belt 24, a plurality of idlers 26 for supporting the return reach 27 of belt 24, a tail pulley 29, and a head pulley 30. Conveyor belt 24 may be driven (in the direction as indicated in FIG. 1) by way of head pulley 30, through a gear reducer 31, as operably interconnected, such as by drive belt 32 to drive means 34.

As adapted for stopped belt sampling, drive means 34 may comprise a power train including a drive motor 35 (of suitable horsepower) as operably interconnected to regulator means 36 for driving belt 32. Regulator means 36 may comprise a conventional interrelationship of brake means and clutch means whereby to stop movement of conveyor belt 24 for the taking of a sample therefrom and for restarting movement of the same after such sample has been taken. For instance, such as a pneumatic or solenoid brake means and such as an air or hydraulic clutch means to cushion restarting.

Belt sampler B may include a frame 37 having legs 38 at one end thereof and legs 39 at the other end thereof, respective legs 38 and 39 being positioned in a spaced apart relation so that belt sampler B may be located astraddle of belt conveyor segment A, with the lower ends of legs 38 and legs 39 attached to opposite sides of frame 20 of belt conveyor segment A, and having a pair of horizontal side frame members 40 and 41 interconnected to and extending in a spaced apart relation at the upper portion of respective legs 38 and legs 39; sample taking means 42, which may include plate means 43 and impeller means 44; and contour means 45.

Plate means 43 may comprise side plates 46 and 47, rotatably mounted on shaft 48 in spaced apart juxtaposed relation to provide spaced apart substantially parallel faces which, on rotation thereof about shaft 48, may be moved through the bulk material stream on conveyor belt 24 and segregate therebetween a full cross-cut section increment of such material with parallel sides. Plates 46 and 47 are preferably spaced apart a distance of not less than three times the diameter of the largest piece of bulk material being conveyed on conveyor belt 24.

Impeller means 44 may comprise a sweep arm 49 which may also be rotatably mounted on shaft 48, as positioned between plates 46 and 47 and configured to sweep therebetween to remove from conveyor belt 24 substantially the entirety of the increment of bulk material as segregated therebetween.

Side plates 46 and 47 are preferably of segmented arcuate configuration having an apex portion 50 and an arcuate portion 52 having a radius which substantially conforms to the radius of the arc as circumscribed by the outermost end of sweep arm 49 as it removes bulk material from conveyor belt 24.

Piston means 54 may be mounted on frame 37 and operably interconnected to plate means 43, such as by support 56, for rotation thereof about shaft 48.

Support 56 may comprise a mounting plate interconnected between plates 46 and 47 adjacent apex portions 50 thereof. Piston means 55 may be mounted on support 56 and operably interconnected to impeller means 44 for rotation thereof about shaft 48.

Piston means 54 and 55 are preferably actuated by compressed air, in a manner such that the stroke thereof, through respective operation of plate means 43 and impeller means 44, and return to a rest position takes but a fraction of a second.

Contour means 45 may comprise a pair of spaced apart side plates 58 and 59 which are pivotally mounted at one end thereof on shaft 60. Side plates 58 and 59 are each provided with an arcuate portion 62, to and extending between which is provided support plate means 63 which may define a lift means for receiving and raising a portion of the conveying reach of conveyor belt 24.

Piston means 65 may be mounted on frame 37 and operably interconnected to contour means 45 for pivotally raising and lowering the same about shaft 60.

The configuration of plate means 63 as attached to arcuate portions 62 of side plates 58 and 59 provide a lift means 64 of an arcuate configuration having a radius which substantially conforms to the radius of the arc as circumscribed by the outermost end of sweep arm 49 as it moves between side plates 46 and 47 of plate means 43.

As diagrammatically shown in FIGS. 5–10, and as will subsequently be more fully described, contour means 45 is normally disposed below the conveying reach 23 of conveyor belt 24 and, on actuation of piston means 65 abuts against, lifts, and contours a portion of the conveying reach so that it has a transverse arcuate configuration which substantially conforms to the radius of the arc as circumscribed by the outermost end of sweep arm 49 as it moves between side plates 46 and 47 of plate means 43. Thus, contour means 45 modulates the normal troughing of the conveyor belt in a manner to facilitate a clean sweep of impeller means 44 across the belt and also serves to support the belt in a manner whereby to substantially eliminate the possibility of puncture of the belt by sharp-edged samples as they are being removed therefrom.

An upper guide plate 68 may be mounted on frame 37 and a lower guide plate 69 mounted on contour means 45 for guiding bulk material as removed from conveyor belt 24 by impeller means 44 into an appropriate holding vessel such as a suitable hopper for grading thereof.

Control means 72 may be mounted on frame 37 for systematic operation of my improved belt sampler. For instance, when used as a mechanized stopped belt sampler, for sequentially actuating the brake means of regulator means 36 to stop conveyor belt 24; actuating contour means 45 to raise and conform a portion of the conveying reach of conveyor belt 24 to an arcuate configuration which substantially conforms to that radial path as will be followed by impeller means 44; positioning plate means 43 to segregate therebetween an increment 74 of bulk material on conveyor belt 24; actuating impeller means 44 to remove the thus segregated increment of bulk material from conveyor belt 24; returning impeller means 44 and plate means 43 to the initial positions thereof; actuating contour means 45 to lower conveyor belt 24 to its normal conveying position; and releasing the brake means of regulator means 36 and actuating the same to restart conveying movement of conveyor belt 24.

Control means 72 is preferably pre-set in accordance with predetermined timing or location as to sample taking free of selection on a discretionary basis by an operator, and is operative such that the systematic and sequential operation thereof is performed within a very short period of time, preferably less than five seconds. The bulk material receiving end of conveyor belt 24 will normally have, or can easily be retrofitted with, sufficient surge capacity to permit continued feeding of bulk material onto belt conveyor A when conveyor belt 24 thereof is stopped for sampling purposes.

Figures 5, 6, 7, 8, 9, 10:
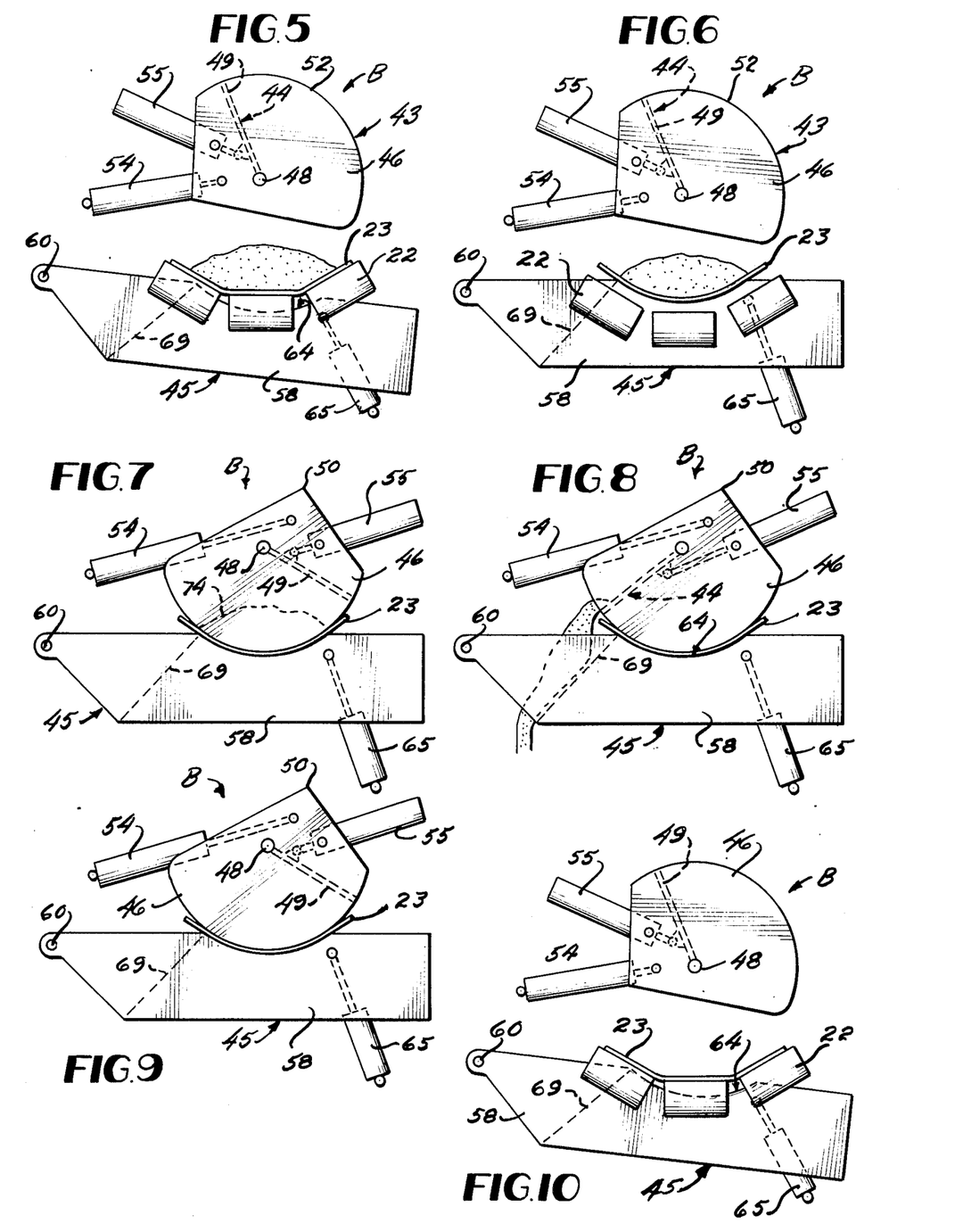
FIGS. 5 through 10 are diagrammatic views showing operation of the belt sampler of FIG. 3.

As previously indicated, the operation of belt sampler B is diagrammatically shown in FIGS. 5 through 10. That is:

FIG. 5—Belt sampler B as positioned during normal conveying operation of belt conveyor A;

FIG. 6—Conveyor belt 24 has been stopped and contour means 45 has lifted and is supporting that segment of conveyor belt 24 from which an increment of bulk material thereof is to be taken and has conformed the same to a transverse arcuate configuration substantially similar to the path that will be taken by impeller 44 in removing an increment of bulk material therefrom;

FIG. 7—Plate means 43 has been rotated such that plates 46 and 47 have segregated therebetween a full cross-section increment of the bulk material on conveyor belt 24;

FIG. 8—Impeller means 44 has moved across conveyor belt 24 and has swept therefrom the increment of bulk material on conveyor belt 24 as segregated between plates 46 and 47;

FIG. 9—Impeller means 44 has been retracted to its at rest position;

FIG. 10—Plate means 43 and contour means 45 have been returned to the same positions thereof as shown in FIG. 5, and movement of conveyor belt 24 has been restarted for normal conveying operation thereof.

The showing of belt sampler C is by way of illustrating that various parts of belt sampler B may be relocated, as desired, without departing from the spirit of my invention. Accordingly, identical reference characters, with a prime superscript, have been applied to corresponding parts of belt sampler C.

As shown in FIG. 11, impeller means 44' may be mounted on shaft 48' for rotation in a counterclockwise direction, piston means 55' for actuation thereof being mounted on frame 37'; contour means 45' may be pivotally mounted on leg 38' of frame 37' rather than on leg 39' thereof; and lift means 64' may comprise a continuous plate means 63'.

Of course, it is obvious that lift means 64 could be mounted astraddle the return reach 27 of the belt conveyor, for lifting in the line of travel of the belt, rather than from one side thereof.

FIG. 12 is a somewhat diagrammatic view as taken toward one side of belt sampler D and FIG. 13 is a somewhat diagrammatic view as taken toward the other side thereof. As to those parts of belt sampler D which correspond to parts of belt sampler B, identical reference characters, with a double prime superscript, have been applied thereto.

As best shown in FIG. 12, an eccentric 80 is attached to shaft 48" for rotation thereof, and plate means 42" is mounted on shaft 48" for rotation therewith. Piston means 54" is mounted on side frame 40" and interconnected to eccentric 80 in a manner such that plate means 42" can be rotated through 360°, as shown by arrow 81 in FIG. 12.

As best shown in FIG. 13, sweep arm 49" is mounted on a sleeve 82 which is rotatably mounted on shaft 48". An eccentric 84 is attached to sleeve 82 for rotation thereof about shaft 48". Piston means 55" is mounted on side frame 41" and interconnected to eccentric 84 in a manner such that sweep arm 49" can be rotated through 360°, as shown by arrow 85 in FIG. 12.

As also shown in FIGS. 12 and 13, contour means 45" may comprise idler roller support means 86, as preferably spaced to each side of and beneath frame 37", each idler roller support means comprising a plurality of idler rollers 87 as substantially catenated between side supports 88 and 89, as respectively mounted on opposite sides of frame 20" of the belt conveyor, and which entrain the conveying reach 23" of the belt conveyor to an arcuate configuration which substantially conforms to the radius of the extremities of the paths circumscribed by plate means 42" and sweep arm 49".

Rotation of plate means 42" and rotation of sweep arm 49" are calibrated for timed movement through the bulk material on conveying reach 23", first to segregate a sample between plate means 42", sweep arm 49" then sweeping the thus segregated sample from conveying reach 23", and, each make but a single pass through the bulk material on conveying reach 23" and thereafter rotating through 360° to their respective starting positions.

In this form of the invention, a grouping comprising a plurality of closely adjacent idler roller support means 86 are provided at the operative course of plate means 43" and impeller means 44". The idlers 22 to the sides of such grouping may be the more conventionally used three roll idlers as shown in FIGS. 1, 2, and 5-10. Of course, idler support means 86 may be disposed so that the lower course thereof is generally in-line with idlers 22, may be positioned on frame 20 to lift conveying reach 23 above the normal course followed by conveyor belt 24, as entrained over idlers 22, or could be mounted on a sub-frame assembly adapted to be vertically raised to engage and lift conveyor belt 24 only during operation of the belt sampler.

Further, it is within the scope of this invention to provide sample taking means 42 as one sub-frame assembly and contour means 45 as another. For instance, as modular units adapted to provide proper dimensional relationships which fit above the belt on the one hand and below the belt on the other.

It is obvious that contour means 45 may be used in association with various types of sample taking means other than that as herein shown and described, and for moving as well as stopped belt sampling.

It is also obvious that various types of drive means may be used for rotating sample taking means 42. That is, by means of pistons which may be mounted on a frame other than as herein shown and described, or such as by a drive motor or other power means for rotation of the shaft, sleeve, or other support on which the sample taking head is mounted and moved across the conveyor belt.

Also, contour means 45 could be stationary, either slightly below or in slight contact with the lower surface of the conveying reach. That is, it is not necessary that the same be articulated up and down into and out of contact with the conveyor belt.

In other words, the essence of this invention is not the particulars of construction, but rather the overall conceptual provision of appropriate sample taking means and contour means by way of which an ASTM Type I increment may be taken according to ASTM Condition A when my belt sampler is operated as a mechanized stopped belt sampler, or an ASTM Type I increment may be taken according to Condition B when my belt sampler is operated as a moving belt sampler.

Various changes may be made in the forms of the invention herein shown and described without departing from the spirit of the invention or the scope of the following claims.

I claim:

1. In combination with a belt conveyor having a conveyor belt for conveying bulk material disposed thereon and drive means for said belt, sample taking means movable across said conveyor belt for removing a cross-stream increment of bulk material therefrom, said sample taking means including plate means for segregating therebetween a cross-stream increment of bulk material as disposed on said conveyor belt and impeller means for removing the thus segregated cross-stream increment of bulk material from said conveyor belt, and contour means for modulating the normal troughing of said conveyor belt and supporting and conforming said conveyor belt to the operative course of said sample taking means as it moves across said conveyor belt.

2. The combination as specified in claim 1 wherein said belt drive means includes brake means for stopping said conveyor belt during operation of said sample taking means and activator means for thereafter restarting movement of said conveyor belt.

3. The combination as specified in either of claims 1 or 2 and wherein said contour means includes plate means normally disposed in a spaced apart position below said conveyor belt, and means for raising said plate means to provide lift means for receiving and raising a portion of the conveying reach of said conveyor belt above the normal conveying reach thereof during operation of said sample taking means.

4. The combination as specified in either of claims 1 or 2 and wherein said contour means includes plate means defining a slideway along which said conveyor belt moves.

5. The combination as specified in either of claims 1 or 2 and wherein said contour means comprises a plurality of closely spaced substantially catenated idler roller support means.

6. A belt conveyor as specified in either of claims 1 or 2 and including control means for timed and sequential operation of said sample taking means absent human discretion.

7. A belt conveyor as specified in either of claims 1 or 2 and wherein said plate means comprises a pair of spaced apart parallel plates for segregating therebetween a full cross-section cut of bulk material, said plates having a conveyor belt engaging extremity of an arcuate configuration, said impeller means being movable with respect to and between said parallel plates and having a belt engaging extremity which follows an arcuate path coincident to the arcuate configuration of the extremity of each of said plates, and wherein said contour means is operable for conforming at least that portion of the bulk material conveying surface of said belt conveyor across which said plate means and said impeller means move to a transversely extending arcuate configuration which is substantially the same as said extremity arcuate configuration of said plates and having a radius which substantially conforms to the arcuate path followed by said extremity thereof as said impeller means moves across said conveyor belt.

8. The method of taking a cross-stream sample increment of bulk material from a conveyor belt and which consists in segregating such increment, sweeping the thus segregated increment from the conveyor belt and supporting and conforming the conveyor belt to the operative course of segregation and sweeping of the increment from the conveyor belt during operation thereof.

9. The method as specified in claim 8 wherein the increment of bulk material is removed from the belt conveyor through a swath having a radial path cross stream of the bulk material of the stopped conveyor belt and wherein at least that portion of the bulk material conveying surface of the conveyor belt cross stream from which the increment is removed is substantially conformed to a transversely extending arcuate configuration having a radius which substantially conforms to the radial path of such a swath.

10. In apparatus for removing samples of bulk material from the conveyor belt of a belt conveyor, the combination of plate means operative to segregate therebetween a cross-stream increment of bulk material as disposed on said conveyor belt, impeller means operative to remove the thus segregated increment of bulk material from said conveyor belt, and contour means for supporting and conforming said conveyor to the operative course of said plate means and said impeller means.

11. The combination as specified in claim 10 and including brake means for stopping said conveyor belt during operation of said plate means and operation of said impeller means, and actuator means for thereafter restarting movement of said conveyor belt.

12. The combination as specified in claim 11 and including control means for timed sequential stopping and restarting of said conveyor belt and for segregating and removing increments of the bulk material from the stopped belt absent human discretion.

13. The combination as specified in either of claims 10 or 11 and wherein said impeller means is operatively movable along a radial path of engagement with said conveyor belt for removing a substantially full cross-section cut of an increment of bulk material from the belt conveyor, said plate means has a conveyor belt engaging terminus of arcuate configuration such that when said plate means is positioned for segregation therebetween of a cross-stream increment of the bulk material of the conveyor belt said terminus of said plate means substantially conforms to the radial path along which said impeller means moves, said impeller means being disposed between said plate means and being configured to cut from the belt conveyor substantially the entirety of the increment of bulk material as disposed on said conveyor belt and segregated between said plate means, and said contour means is operative to conform at least that portion of the bulk material carrying surface of said belt conveyor from which a full cross-section increment of bulk material is cut to a transversely extending arcuate configuration having a radius which substantially conforms to the radial path along which said impeller means operatively moves in removing an increment of bulk material from the stopped belt conveyor.

14. The combination as specified in claim 13 and wherein said contour means comprises lift means for raising and supporting at least that portion of said conveyor belt from which an increment of bulk material is to be taken from the normal conveying reach thereof and contouring the same from the normal transverse conveying contour thereof to said transversely extending arcuate configuration.

* * * * *